United States Patent
Hong et al.

(10) Patent No.: US 10,308,937 B2
(45) Date of Patent: Jun. 4, 2019

(54) COMBINATION LONG ACTING COMPOSITIONS AND METHODS FOR HEPATITIS C

(71) Applicant: GlaxoSmithKline Intellectual Property (No. 2) Limited, Brentford, Middlesex (GB)

(72) Inventors: Zhi Hong, Research Triangle Park, NC (US); Martin R. Leivers, Research Triangle Park, NC (US)

(73) Assignee: GlaxoSmithKline Intellectual Property (No. 2) Limited (GB)

( * ) Notice: Subject to any disclaimer, the term of this patent is extended or adjusted under 35 U.S.C. 154(b) by 0 days.

(21) Appl. No.: 15/525,926

(22) PCT Filed: Oct. 30, 2015

(86) PCT No.: PCT/IB2015/058423
§ 371 (c)(1),
(2) Date: May 10, 2017

(87) PCT Pub. No.: WO2016/075584
PCT Pub. Date: May 19, 2016

(65) Prior Publication Data
US 2017/0314022 A1    Nov. 2, 2017

Related U.S. Application Data

(60) Provisional application No. 62/077,980, filed on Nov. 11, 2014, provisional application No. 62/077,647, filed on Nov. 10, 2014.

(51) Int. Cl.
| | | |
|---|---|---|
| C07H 21/02 | (2006.01) |
| C07H 21/04 | (2006.01) |
| A61K 48/00 | (2006.01) |
| C12N 15/113 | (2010.01) |
| A61K 9/00 | (2006.01) |
| A61K 47/26 | (2006.01) |
| A61K 45/06 | (2006.01) |
| A61K 47/10 | (2017.01) |
| A61K 31/7105 | (2006.01) |
| A61K 9/50 | (2006.01) |
| A61K 31/4178 | (2006.01) |
| A61K 31/4184 | (2006.01) |
| A61K 31/4188 | (2006.01) |
| A61K 31/439 | (2006.01) |
| A61K 31/4709 | (2006.01) |
| A61K 31/506 | (2006.01) |
| A61K 31/519 | (2006.01) |
| A61K 31/549 | (2006.01) |
| A61K 31/69 | (2006.01) |
| A61K 31/7068 | (2006.01) |
| A61K 31/7072 | (2006.01) |
| A61K 47/32 | (2006.01) |

(52) U.S. Cl.
CPC ........ *C12N 15/1131* (2013.01); *A61K 9/0019* (2013.01); *A61K 9/5031* (2013.01); *A61K 31/4178* (2013.01); *A61K 31/4184* (2013.01); *A61K 31/4188* (2013.01); *A61K 31/439* (2013.01); *A61K 31/4709* (2013.01); *A61K 31/506* (2013.01); *A61K 31/519* (2013.01); *A61K 31/549* (2013.01); *A61K 31/69* (2013.01); *A61K 31/7068* (2013.01); *A61K 31/7072* (2013.01); *A61K 31/7105* (2013.01); *A61K 45/06* (2013.01); *A61K 47/10* (2013.01); *A61K 47/26* (2013.01); *A61K 47/32* (2013.01); *C12N 2310/113* (2013.01); *C12N 2310/351* (2013.01); *C12N 2320/31* (2013.01)

(58) Field of Classification Search
CPC .......................... A61K 31/713; C12N 15/111
See application file for complete search history.

(56) References Cited

U.S. PATENT DOCUMENTS

2010/0239529 A1 * 9/2010 Del Rio et al. ...... C12N 15/113
2013/0287836 A1 * 10/2013 Ingber et al. ........ A61K 31/713

FOREIGN PATENT DOCUMENTS

| WO | 2012/175733 A1 | 12/2012 |
| WO | 2013/000855 A1 | 1/2013 |
| WO | 2013/000856 A1 | 1/2013 |
| WO | 2014/118272 A1 | 8/2014 |
| WO | 2014/179446 A2 | 11/2014 |
| WO | WO 2014/179446 | * 11/2014 ........... C12N 15/111 |

OTHER PUBLICATIONS

Bhat, et al., "RG-101, a GaINAc-conjugated anti-miR EMploying a Unique Mechanism of Action by Targeting Host Factor MicroRNA-122 (miR-122), Demonstrates Potent Activity and Reduction of HCV in Preclinical Studies." http://www.regulusrx.com/wp-content/uploads/2013/11/RT13-002-Neben_AASLD-LFP_final.pdf;2013.

* cited by examiner

*Primary Examiner* — Amy H Bowman
(74) *Attorney, Agent, or Firm* — Barbara J. Carter

(57) ABSTRACT

The present Invention relates to pharmaceutical compositions useful in the treatment or prevention or cure of viral infections, such as HCV infections, and diseases associated with such infections.

24 Claims, 5 Drawing Sheets
Specification includes a Sequence Listing.

FIGURE 1

Mean Rat Pharmacokinetics of Two Formulations of LAP HCV active agent Dosed Intramuscular (IM) and Subcuten

FIGURE 2

Dog Pharmacokinetics of a Poloxamer 188 based Formulation of LAP HCV active agent Dosed Intramuscular (IM) at 100 mg/kg

FIGURE 3

Dog Pharmacokinetics of a Poloxamer 188 based Formulation of LAP HCV active agent Dosed Intramuscular (IM) at 100 mg/kg

FIGURE 4

Dog Pharmacokinetics of a Tween-20 based Formulation of LAP HCV active agent
Dosed Intramuscular (IM) at 10 mg/kg

FIGURE 5

Dog Pharmacokinetics of a Tween 80 Formulation of LAP HCV active agent Dosed Intramuscular (IM) at 10 mg/kg

US 10,308,937 B2

SEQUENCE LISTING

```
<160> NUMBER OF SEQ ID NOS: 2

<210> SEQ ID NO 1
<211> LENGTH: 31
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1
agacacaaac accauuguca cacuccacag c                                    31

<210> SEQ ID NO 2
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2
acaaacacca uugucacacu cca                                             23
```

COMBINATION LONG ACTING COMPOSITIONS AND METHODS FOR HEPATITIS C

CROSS-REFERENCE TO RELATED APPLICATIONS

This application is filed pursuant to 35 U.S.C. § 371 as a United States National Phase Application of International Application No. PCT/IB2015/058423 filed Oct. 30, 2015 which claims priority from U.S. Provisional No. 62/077647 filed Nov. 10, 2014 and U.S. Provisional No. 62/077980 filed Nov. 11, 2014.

FIELD OF THE INVENTION

The present invention relates to long acting parenteral (LAP) formulations of anti-viral agents, specifically Hepatitis C Virus (HCV) inhibitors in combination with other HCV active treatment agents as well as methods of treating or preventing or curing viral infections, such as HCV infections, and diseases associated with such infections.

BACKGROUND OF THE INVENTION

Infection with HCV is a major cause of human liver disease throughout the world. Chronic infection with HCV is associated with chronic liver disease, cirrhosis, hepatocellular carcinoma, and liver failure. HCV is a hepacivirus member of the Flaviviridae family of RNA viruses that affect animals and humans. The genome is a single ~9.6-kilobase strand of RNA, and consists of one open reading frame that encodes for a polyprotein of ~3000 amino acids flanked by untranslated regions at both 5' and 3' ends (5'- and 3'-UTR). The polyprotein serves as the precursor to at least 10 separate viral proteins critical for replication and assembly of progeny viral particles. The organization of structural and non-structural proteins in the HCV polyprotein is as follows: C-E1-E2-p7-NS2-NS3-NS4a-NS4b-NS5a-NS5b. While the pathology of HCV infection affects mainly the liver, the virus is found in other cell types in the body including peripheral blood lymphocytes.

HCV is a major causative agent for post-transfusion and for sporadic hepatitis. Infection by HCV is insidious in a high proportion of chronically infected, and infectious, carriers who may not experience clinical symptoms for many years. An estimated 170 million chronic carriers worldwide are at risk of developing liver disease.

Due to the high degree of variability in the viral surface antigens, existence of multiple viral genotypes, and demonstrated specificity of immunity, the development of a successful vaccine in the near future is unlikely. Alpha-interferon, alone or in combination with ribavirin, has been widely used for treatment of chronic HCV infection. However, treatment of HCV with interferon has frequently been associated with adverse side effects such as fatigue, fever, chills, headache, leukopenia, thrombocytopenia, psychiatric effects and associated disorders, autoimmune phenomena and associated disorder and thyroid dysfunction. Ribavirin, an inhibitor of inosine 5'-monophosphate dehydrogenase (IMPDH), enhances the efficacy of IFN-alpha in the treatment of HCV. Despite the introduction of ribavirin, more than 50% of the patients do not eliminate the virus with the current therapy of interferon-alpha (IFN) and ribavirin. With the introduction of pegylated interferon, both initial and sustained response rates have improved, and combination treatment of Peg-IFN with ribavirin until recently, constituted a standard for therapy. However, the side effects associated with combination therapy persist. Ribavirin causes significant hemolysis in 10-20% of patients treated at currently recommended doses, and the drug is both teratogenic and embryotoxic.

Most recently, oral agents including Sofosbuvir were introduced as a component of a combination antiviral regimen for patients with HCV mono-infection and HCV/HIV-1 coinfection. Treatment regimen and duration are dependent on both viral genotype and patient population and can vary from 8 to 24 weeks. Consequently, a prescribed treatment requires ingestion of a daily regimen which can lead to reduced patient compliance resulting in reduced drug efficacy and development of resistant strains of HCV. In highly motivated populations, adherence to these shorter duration therapies can be good and cure rates can be very high. In marginal populations such as IV drug abusers, the homeless, and the mentally ill, adherence to regimens may be poorer and a lack of adherence may result in treatment failure and development of long-lived resistance mutations in the HCV genome. Additionally for some populations, such as incarcerated patients, the associated cost of each treatment (dose) may be very high.

Accordingly, successful long acting treatments for HCV infected patients which reduce the number of treatments down to even a single treatment can alleviate compliance issues and issues associated with the cost of treatment This would represent a significant advance for HCV patients.

SUMMARY OF THE INVENTION

The present invention addresses the issue of non-compliance as well as treatment of resistant strains of HCV by formulating one or more HCV active agents as a LAP composition suitable for administration, for example, once, once per month, once every 2 months, once every 3 months, once every 6 months or once every 12 months, in combination with the compounds of Formula IIA or IIB.

In a first aspect of the present invention, there is provided a LAP pharmaceutical composition including at least one HCV active agent or a pharmaceutically acceptable salt thereof, in combination with a LAP HCV active agentIA or IIB.

In a second aspect of the present invention, there is provided a method for the treatment or cure of an HCV infection in a human having an HCV infection including administering to the human a LAP pharmaceutical composition including at least one HCV active agent or a pharmaceutically acceptable salt thereof, in combination with a LAP HCV active agentIA or IIB.

In a third aspect of the present invention, there is provided use of a LAP pharmaceutical composition including at least one HCV active agent or a pharmaceutically acceptable salt thereof, in combination with a LAP HCV active agentIA or IIB, for use in medical therapy.

In a fourth aspect of the present invention, there is provided the use of at least one HCV active agent or a pharmaceutically acceptable salt thereof in the preparation of a long acting parenteral medicament in combination with a LAP HCV active agentIA or IIB, for use in the treatment of HCV infection in a human.

In a fifth aspect of the present invention there is provided a method for the treatment or cure or treatment to achieve a cure of an HCV infection in a human having an HCV infection comprising administering to the human a LAP pharmaceutical composition comprising a first unit dosage of at least one HCV active agent, or a pharmaceutically acceptable salt thereof; and a second unit dosage of a LAP HCV active agentIA or IIB, anti-microRNA compounds that are complementary to microRNA 122 (miR122) and are known as anti-miR122 compounds or anti-mir-122 oligonucleotides.

IIA

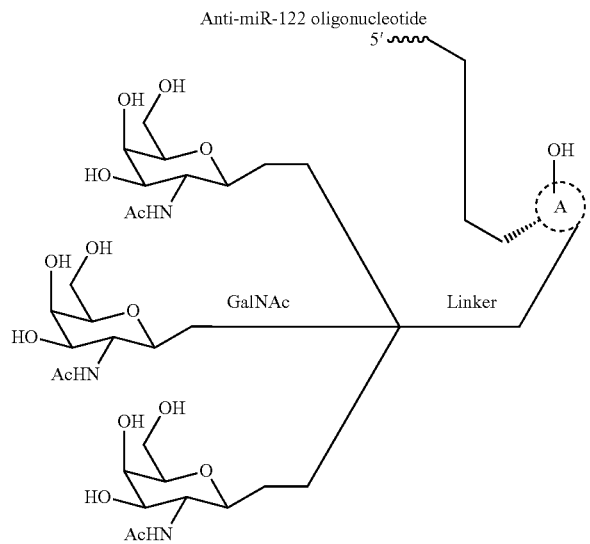

IIB

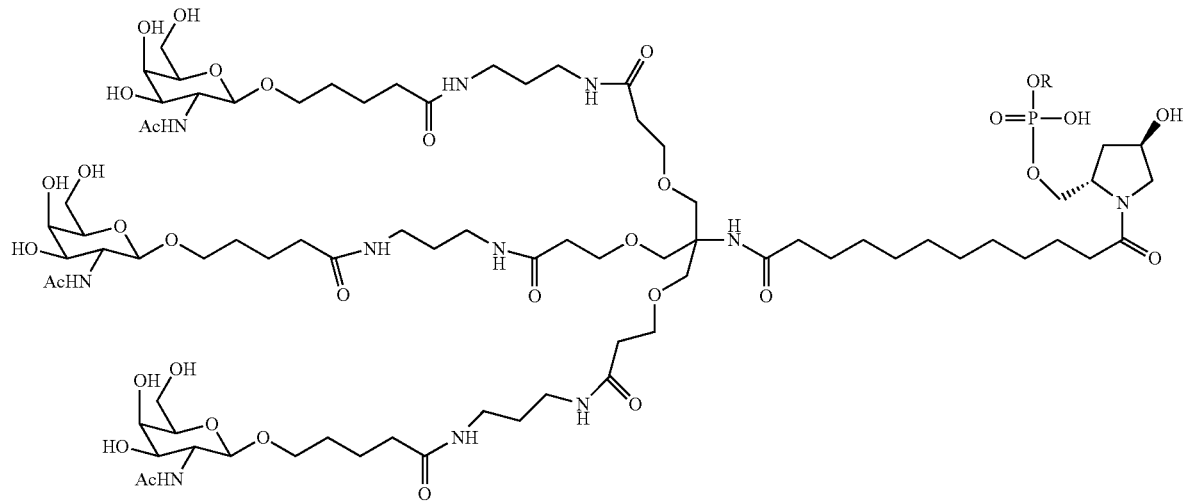

wherein R =

, or

5′-3′ anti-miR-122 oligonucleotide-wherein the first and second unit dosages are administered separately or together, and wherein the first and second unit dosages are administered serially or simultaneously; and in some embodiments, the method of treating Hep C may also encompass a method of curing Hep C in a human after only one administration of Formula IIA or Formula IIB and the HCV active agent.

One particular embodiment of the invention provides compounds of Formula IIA and IIB. Such compounds are In another particular embodiment, compounds of Formula IIA or IIB may be used, in combination with other LAP HCV active agents, in the treatment or prevention or cure of an HCV infection in a human. The combinations may be administered in separate formulations, at separate times; the combinations of a LAP HCV active agent and a LAP HCV active agentIA or Formula IIB may be administered in separate formulations as separate unit dosages, and may be administered serially, simultaneously; in addition, the combinations of a LAP HCV active agent and a LAP HCV active agentIA or Formula IIB may be administered in a single pharmaceutical formulation; and/or the combination may be administered in a fixed dose combination.

In certain embodiments, the anti-miR-122 oligonucleotide of Formula IIA or Formula IIB comprises at least one modified internucleoside linkage, modified sugar moiety, or modified nucleobase. In certain embodiments the anti-miR-122 oligonucleotide of Formula IIA or Formula IIB comprises at least one 2'-O-methoxyethyl sugar moiety. In certain embodiments the anti-miR-122 oligonucleotide of Formula IIA or Formula IIB comprises at least one phosphorothioate internucleoside linkage. In certain embodiments the anti-miR-122 oligonucleotide of Formula IIA or Formula IIB comprises at least one 5-methylcytosine. In certain embodiments the anti-miR-122 oligonucleotide of Formula IIA or Formula IIB comprises a phosphorothioate internucleoside linkage and comprises at least one 5-methylcytidine. In certain embodiments the anti-miR-122 oligonucleotide of Formula IIA or Formula IIB comprises at least one constrained ethyl moiety.

In particular embodiments, ring A of Formula IIA may be independently selected from cycloalkyl or heterocyclyl.

BRIEF DESCRIPTION OF THE DRAWINGS

FIG. 1 depicts a plot of mean blood concentration of two LAP formulations of a LAP HCV active agent versus time in hours in rat (intramuscular—IM and subcutaneous—SC).

FIG. 2 depicts a plot of individual blood concentrations of a micronised Poloxamer 188 LAP formulation of a LAP HCV active agent at 100 mg/kg versus time in hours in dog (intramuscular—IM).

FIG. 3 depicts a plot of individual blood concentrations of a nanosized Poloxamer 188 LAP formulation of a LAP HCV active agent at 100 mg/kg versus time in hours in dog (intramuscular—IM).

FIG. 4 depicts a plot of individual blood concentrations of a micronized Tween 20 LAP formulation of a LAP HCV active agent at 10 mg/kg versus time in hours in dog (intramuscular—IM).

FIG. 5 depicts a plot of individual blood concentrations of a nanosized Tween 80 LAP formulation of a LAP HCV active agent at 10 mg/kg versus time in hours in dog (intramuscular—IM).

DETAILED DESCRIPTION OF THE INVENTION

Definitions: As used herein, "cycloalkyl" refers to non-aromatic carbocycles including cyclized alkenyl, and alkynyl groups. Cycloalkyl groups can include mono- or polycyclic (e.g., having 2, 3 or 4 fused rings) ring systems, including spirocycles. In some embodiments, cycloalkyl groups can have from 3 to about 20 carbon atoms, 3 to about 14 carbon atoms, 3 to about 10 carbon atoms, or 3 to 7 carbon atoms. Cycloalkyl groups can further have 0, 1, 2, or 3 double bonds and/or 0, 1, or 2 triple bonds. Also included in the definition of cycloalkyl are moieties that have one or more aromatic rings fused (i.e., having a bond in common with) to the cycloalkyl ring, for example, benzo derivatives of pentane, pentene, hexane, and the like. One or more ring-forming carbon atoms of a cycloalkyl group can be oxidized, for example, having an oxo or sulfide substituent. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like.

As used herein, "heterocyclyl" or "heterocycle" refers to a saturated or unsaturated cyclic group wherein one or more of the ring-forming atoms is a heteroatom such as O, S, or N. Heterocyclyl groups include mono- or polycyclic ring systems. Heterocyclyl groups can be aromatic (e.g., "heteroaryl") or non-aromatic (e.g., "heterocycloalkyl"). Heterocyclyl groups can be characterized as having 3-14, 3-12, 3-10, 3-7, or 3-6 ring-forming atoms. In some embodiments, heterocyclyl groups can contain, in addition to at least one heteroatom, from about 1 to about 13, about 2 to about 10, or about 2 to about 7 carbon atoms and can be attached/linked through either a carbon atom or a heteroatom. In further embodiments, the heteroatom can be oxidized (e.g., have an oxo or sulfido substituent) or a nitrogen atom can be quaternized. Examples of heterocyclyl groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like, as well as any of the groups listed below for "heteroaryl" and "heterocycloalkyl." Further example heterocycles include pyrimidinyl, phenanthridinyl, phenanthrolinyl, phenazinyl, phenothiazinyl, phenoxathiinyl, phenoxazinyl, phthalazinyl, piperazinyl, piperidinyl, 3,6-dihydropyridyl, 1,2,3,6-tetrahydropyridyl, 1,2,5,6-tetrahydropyridyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrazolyl, 6H-1,2,5-thia-diazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl, octahydro-isoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, quinazolinyl, quinolinyl, 4H-quinolizinyl, quinoxalinyl, quinuclidinyl, acridinyl, azocinyl, benzimidazolyl, benzofuranyl, benzothiofuranyl, benzo-thiophenyl, benzoxazolyl, benzthiazolyl, benztriazolyl, benztetrazolyl, benzisoxazolyl, benzisothiazolyl, benzimidazolinyl, methylenedioxyphenyl, morpholinyl, naphthyridinyl, deca-hydroquinolinyl, 2H,6H-1,5,2dithiazinyl, dihydrofluro[2,3-b]tetrahydrofuran, furanyl, furazanyl, carbazolyl, 4aH-carbazolyl, carbolinyl, chromanyl, chromenyl, cinnolinyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl and isoxazolyl. Further examples of heterocycles include azetidin-1-yl, 2,5-dihydro-1H-pyrrol-1-yl, piperindin-1-yl, piperazin-1-yl, pyrrolidin-1-yl, isoquinol-2-yl, pyridin-1-yl, 3,6-dihydropyridin-1-yl, 2,3-dihydroindol-1-yl, 1,3,4,9-tetrahydrocarbolin-2-yl, thieno[2,3-c]pyridin-6-yl, 3,4,10,10a-tetrahydro-1H-pyrazino[1,2-a]indol-2-yl, 1,2,4,4a,5,6-hexahydro-pyrazino[1,2-a]quinolin-3-yl, pyrazino[1,2-a]quinolin-3-yl, diazepan-1-yl, 1,4,5,6-tetrahydro-2H-benzo[f]isoquinolin-3-yl, 1,4,4a,5,6,10b-hexahydro-2H-benzo[f]isoquinolin-3-yl, 3,3a,8,8a-tetrahydro-1H-2-aza-cyclopenta[a]inden-2-yl, and 2,3,4,7-tetrahydro-1H-azepin-1-yl, azepan-1-yl.

Hepatitis C virus is a positive strand RNA virus. The key enzyme for HCV RNA synthesis is NS5B, the RNA-dependent RNA polymerase that replicates the viral genome.

NS5B works in a membrane-associated complex that also contains NS4A, NS4B, NS3 protease-helicase and NS5A. These subunits can recognize cis-acting regulatory sequences in the HCV genome. These proteins also have some additional roles during the infection process that are independent of RNA synthesis. Therefore, targeting the viral replication enzymes could prevent the virus from affecting normal cellular processes as well as inhibiting HCV RNA synthesis.

Harvoni® is a recently approved combination of the NS5B polymerase inhibitor Sofosbuvir coformulated with the NS5A inhibitor ledipisvir for the treatment of HCV genotypes 1. Phase 3 trials of Harvoni® involving patients with HCV alone have demonstrated it to be effective when used for 8-24 weeks for HCV genotype 1. Other combinations of oral agents such as Sofosbuvir and ribavirin have been shown to be effective in treating other genotypes of HCV. Although there are effective treatment regimens, they all require daily ingestion which can lead to reduced patient compliance resulting in reduced drug efficacy and resistance.

6-(N-(7-chloro-1-hydroxy-1,3-dihydrobenzo[c][1,2]oxaborol-5-yl)methylsulfonamido)-5-cyclopropyl-2-(4-fluorophenyl)-N-methylbenzofuran-3-carboxamide which is a LAP HCV active agent,

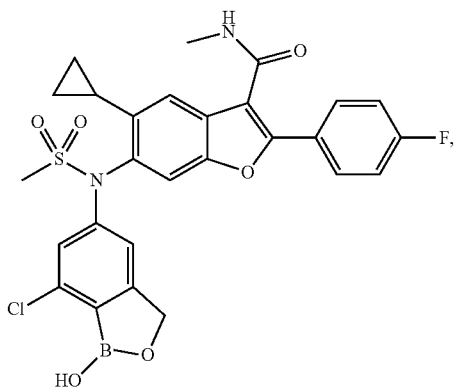

and is an NS5B polymerase inhibitor that is currently being developed for the treatment of HCV infection and associated disease states.

The present invention addresses ease of treatment and non-compliance issues in the treatment of HCV by formulating a LAP HCV active agent, including 6-(N-(7-chloro-1-hydroxy-1,3-dihydrobenzo[c][1,2]oxaborol-5-yl)methylsulfonamido)-5-cyclopropyl-2-(4-fluorophenyl)-N-methylbenzofuran-3-carboxamide (a LAP HCV active agent) as a long-acting parenteral (LAP) composition or depot formulation suitable for administration, for example, once, once per week, once every two weeks, once per month, once every 2 months, once every 3 months, once every 6 months or once every 12 months. Such LAP compositions comprising a LAP HCV active agent can also be administered close in time to a second composition comprising the compounds of Formula IIA or Formula IIB.

Long-acting parenteral formulations of LAP HCV active agents could generate sustained effective inhibitory concentrations with infrequent dosing and may improve adherence to therapy. Next to facilitating maintenance of viral suppression following traditional anti-HCV therapy, a long-acting formulation, may also serve as a practical opportunity for pre-exposure prophylaxis.

The present invention features pharmaceutical compositions comprising an active ingredient which is a LAP HCV active agent, or a pharmaceutically acceptable salt thereof, suitable for administration once, once monthly or longer, that is also optionally administered in combination (separately or together) with any of the compounds of Formula IIA or IIB, to a patient having an HCV infection.

The present invention is expected to result in prolonged plasma exposure of one or more HCV LAP active agents I at concentrations above that minimally required for suppression of the HCV virus from a single treatment. With prolonged suppression of the virus, normally longer than 6 weeks, a sustained virologic response can be achieved resulting in functional cure of HCV. The single treatment may be comprised of single or multiple injections (e.g., 1, 2, 3 or 4 injections) given within a short period of time, say less than one hour and can also be administered in combination with the compounds of Formula IIA or IIB. Reducing the treatment phase to a single day results in significant advantages including assured compliance with the full curative regimen, reduced healthcare utilization and allowance of a test and treat paradigm.

Further features of the present invention are methods of using these pharmaceutical compositions.

In one embodiment, the present invention features pharmaceutical compositions, comprising a LAP HCV active agent, or a pharmaceutically acceptable salt thereof, and a surfactant system.

Pharmaceutically acceptable salts include, but are not limited to those described in PCT Published Application No. WO2013028371 deriving from U.S. Provisional Application 61/525,440, filed Aug. 19, 2011.

The term "therapeutically effective amount," as used herein, means a sufficient amount of a drug, compound, composition, product or pharmaceutical agent to abate or reverse or treat a malady in a human or other mammal.

The present invention features parenteral pharmaceutical compositions for administration to a subject, for example a human.

In another embodiment, the present invention features long-acting parenteral pharmaceutical compositions comprising a LAP HCV active agent or a pharmaceutically acceptable salt thereof, and a surfactant system for weekly (once every week) administration.

In another embodiment, the present invention features long-acting parenteral pharmaceutical compositions comprising a LAP HCV active agent or a pharmaceutically acceptable salt thereof, and a surfactant system for bi-weekly (once every two weeks) administration.

In another embodiment, the present invention features long-acting parenteral pharmaceutical compositions comprising a LAP HCV active agent or a pharmaceutically acceptable salt thereof, and a surfactant system for once monthly administration.

In another embodiment, the present invention features long-acting parenteral pharmaceutical compositions comprising a LAP HCV active agent or a pharmaceutically acceptable salt thereof, and a surfactant system for bi-monthly (once every two months) administration.

In another embodiment, the present invention features long-acting parenteral pharmaceutical compositions comprising a LAP HCV active agent or a pharmaceutically acceptable salt thereof, and a surfactant system for tri-monthly (once every three months) administration.

In another embodiment, the present invention features long-acting parenteral pharmaceutical compositions comprising a LAP HCV active agent or a pharmaceutically acceptable salt thereof, and a surfactant system administration once every six or twelve months, or any time point within this range.

The compositions of the present invention provide for the slow release of a LAP HCV active agent over an extended period of time within the body of a subject. Therefore, in order to achieve therapeutic levels of drug, a LAP HCV active agent advantageously is released from the composition within approximately one to three months, or any time point within this range.

An embodiment of the present invention is a pharmaceutical composition suitable for parenteral administration comprising a LAP HCV active agent and a surfactant system comprising a combination of polymers providing for the release of a LAP HCV active agent over a period of one week to three months. A suitable combination of polymers is, for example, polysorbate 80 and polyvinylpyrrolidone (PVP).

The compositions of the present invention may be administered to the subject by various routes, including intramuscular (IM), intravenous (IV), or subcutaneous (SC). Therefore, in one embodiment, the compositions of the present invention are administered to a subject by an intramuscular route. In another embodiment, the compositions of the present invention are administered to a subject by an intravenous route. In another embodiment, the compositions of the present invention are administered to a subject by a subcutaneous route.

For purposes of the present invention, a "surfactant system" means any formulation suitable for pharmaceutical purposes that includes at least one surfactant. For example, a surfactant system that can be used with the present invention may include, in addition to a surfactant, additional components such as buffers, polymers (for drug particles), wetting agents, stabilizers, tonicity modifiers, and solvents such as water.

The surfactant system may include any surfactant as long as it is compatible with pharmaceutical applications. For example, suitable surfactants include, but are not limited to, polyoxyethylene sorbitan fatty acid esters (polysorbates such as polysorbate 20 or 80), poloxamers (such as LUTROL™ F68, F108 and F127 which are block copolymers of ethylene oxide and propylene oxide, sodium dodecylsulfate and/or sodium lauryl sulphate), sorbitan esters of fatty acids (SPAN), polyethoxylated castor oil and its derivatives, tocopheryl polyethylene glycol succinate, and polyvinyl alcohols. In certain embodiments, the surfactant system comprises an amount of surfactant that ranges from about 0.01% (w/v) to about 5% (w/v) surfactant. In other embodiments, the surfactant system comprises an amount of surfactant that ranges from about 0.1% (w/v) to about 3% (w/v) surfactant. In still other embodiments, the surfactant system comprises about 0.2% (w/v) surfactant. In still other embodiments, the surfactant system comprises about 0.4% (w/v) surfactant. In other embodiments, the surfactant system comprises polysorbate-80 (e.g., Tween-80). In still other embodiments, the surfactant system comprises 0.4% (w/v) polysorbate-80.

Representative stabilizers include, but are not limited to, polyethylene glycols, carboxymethylcellulose calcium, carboxymethylcellulose sodium, methylcellulose, hydroxyethylcellulose, hydroxypropylcellulose, hydroxymethylpropylcellulose, polysaccharides, hyarluronic acid, polyvinyl alcohol (PVA) and polyvinylpyrrolidone (PVP). In certain embodiments, the surfactant system comprises an amount of stabilizer that ranges from about 0.01% (w/v) to about 5% (w/v) stabilizer. In other embodiments, the surfactant system comprises an amount of stabilizer that ranges from about 1% (w/v) to about 5% (w/v) stabilizer. In other embodiments, the surfactant system comprises an amount of stabilizer that ranges from about 1% (w/v) to about 3% (w/v) stabilizer. In still other embodiments, the surfactant system comprises about 2% (w/v) stabilizer. In other embodiments, the surfactant system comprises polyethylene glycols. In other embodiments, the surfactant system comprises PEG-3350. In still other embodiments, the surfactant system comprises 2% (w/v) PEG-3350.

Suitable buffer salts include, but are not limited to, buffer salts selected from phosphate salts, citrate salts, acetate salts, and tartrate salts, etc. In certain embodiments, the surfactant system comprises an amount of buffer salts that ranges from about 1 mM to about 100 mM buffer salt. In other embodiments, the surfactant system comprises an amount of buffer salts that ranges from about 2 mM to about 50 mM buffer salt. In other embodiments, the surfactant system comprises an amount of buffer salts that ranges from about 3 mM to about 25 mM buffer salt. In other embodiments, the surfactant system comprises an amount of buffer salts that ranges from about 5 mM to about 15 mM buffer salt. In still other embodiments, the surfactant system comprises about 10 mM buffer salt. In certain embodiments, the pH of the buffer salt is adjusted to range from about pH 6.0 to about pH 8.0. In other embodiments, the pH of the buffer salt is adjusted to range from about pH 6.5 to about pH 7.5. In other embodiments, the pH of the buffer salt is adjusted to range from about pH 6.7 to about pH 7.3. In one embodiment, the buffer salt comprises phosphate buffered saline (PBS). In another embodiment, the buffer salt comprises phosphate buffered saline at a concentration of about 10 mM. In another embodiment, the buffer salt comprises phosphate buffered saline at a concentration of about 10 mM and a pH of about 6.9.

Suitable tonicity modifiers include, but are not limited to, sodium chloride, mannitol, sucrose, maltose, and dextrose, etc. In one embodiment, the tonicity modifier comprises sodium chloride. In another embodiment, the tonicity modifier is sodium chloride. In certain embodiments, the surfactant system comprises a concentration of tonicity modifier that ranges from about 0 to about 350 mM. In certain embodiments, the surfactant system comprises a concentration of tonicity modifier that ranges from about 0 to about 175 mM. In certain embodiments, the surfactant system has a tonicity that ranges from about 250 to about 350 mOsmol/kg.

In one embodiment, a LAP HCV active agent can be suspended as microparticles in a surfactant system and aqueous buffer. In some embodiments, a LAP HCV active agent can be in an amorphous form or in a crystalline form. Typically, the drug particle size ($D_{50}$) will range from about 0.05 μm to about 100 μm. In other embodiments, the drug particle size will range from about 0.1 μm to about 50 μm. In other embodiments, the drug particle size will range from about 0.1 μm to about 20 μm. In other embodiments, the drug particle size ($D_{50}$) will range from about 0.1 μm to about 10 μm. In other embodiments, the drug particle size ($D_{50}$) will range from about 0.1 μm to about 5 μm. In other embodiments, the drug particle size ($D_{50}$) will range from about 1 μm to about 5 μm. In other embodiments, the drug particle size ($D_{50}$) will range from about 0.05 μm to about 0.05 μm. In other embodiments, the drug particle size ($D_{50}$) will range from about 0.5 μm to about 5 μm. In other embodiments, the drug particle size ($D_{50}$) will range from about 5 µm to about 25 µm. In other embodiments, the drug particle size ($D_{50}$) will range from about 25 µm to about 100 µm.

In still other embodiments, the drug particle size in the surfactant system can be mixed sizes. For example, having substantially different particle sizes from relatively large to relatively small, can achieve acceptable pharmacokinetic parameters for the formulation because the small particles are absorbed and metabolized quicker than the larger particles. This type of mixed particle size formulation could enhance the long acting nature of the present invention by providing a quicker release of drug to the subject early after administration while still maintaining a long acting release of the drug at distant times after administration. Therefore, in one embodiment, the present LAP invention could comprise two or more substantially different particle sizes that would allow for earlier and later release of a LAP HCV active agent and such differing absorption kinetics would be a means of enhancing a durable long acting drug exposure. In one embodiment, a LAP HCV active agent is in a microparticle form, wherein the microparticles of a LAP HCV active agent range in size from about 0.05 µm to about 100 µm, wherein said microparticles comprise two or more substantially different particle sizes.

In still other embodiments, the drug particles of a LAP HCV active agent are encapsulated into polymer based microparticles that can, optionally, be subsequently freeze dried for extended storage. When the term "encapsulated" is used with regards to the present invention, it is meant that a LAP HCV active agent is substantially surrounded by a polymer even though some compound may still be present on the surface of the encapsulated compound/polymer structure. Immediately before use, the dry microparticles can optionally suspended in an aqueous buffer solution. The polymers used to prepare such microparticles can be selected from a series of biodegradable polymers including poly (lactic-co-glycolic) acid ($M_w$ 5-200 kD) and its derivatives, such as polyethylene glycol based amphiphilic polymers, etc. The microparticle size ($D_{50}$) could range from about 1 µm to about 100 µm and the drug encapsulation could range from about 10% to about 70% (w/w). In one embodiment, the drug particles of a LAP HCV active agent are encapsulated into polymer based microparticles such as those containing Resomer™. In another embodiment, the drug particles of a LAP HCV active agent are encapsulated into polymer based microparticles such as those containing Resomer™ 752S.

In other embodiments, in-situ gels could be used to encapsulate a LAP HCV active agent. This could be a water-miscible organic solvent-based solution that contains both a LAP HCV active agent and a gel-forming polymer that is water-insoluble. Once administrated (IM or SC), the organic solvent dissipates away and the water-insoluble polymer precipitates out to form the gel containing a LAP HCV active agent. A LAP HCV active agent would then slowly diffuse out as the polymer-based gel degrades in body. The polymers used to prepare in-situ gels are selected from a series biodegradable polymers including poly (lactic-co-glycolic) acid ($M_w$ 5-200 kD) and its derivatives, poly-ethylene glycol based amphiphilic polymers, etc. The organic solvents are selected from N-methyl pyrrolidone (NMP), dimethylsulfoxide (DMSO), dimethylformamide (DMF), dimethylacetamie (DMA), etc. The concentration of the polymer in the organic solvent could be between 1-50% (w/w) and a LAP HCV active agent concentration could be between 1-50% (w/w).

Alternatively, the microparticle formulation can be made through spray-drying process. Similarly, the organic solution containing both a LAP HCV active agent and the selected polymer prepared as described herein is subjected to a spray-drying process where the organic solvent is rapidly evaporated under nitrogen gas flow to form a LAP HCV active agent encapsulated microparticles. The drying temperature is no less than 35C and the solution spray rate is no less than 0.1 ml/min. For the in-situ gel microparticles, a LAP HCV active agent and the selected polymer could be co-dissolved into the suitable organic solvent wherein the organic solvent must meet the following criteria: a) has a good solubility for the selected polymer; b) has a good miscibility with aqueous solution; and c) has a low toxicity and demonstrated safety when use in human; for example N-methyl pyrrolidone (NMP), dimethylsulfoxide (DMSO), dimethylformamide (DMF), dimethylacetamie (DMA), etc. The resulted solution containing both a LAP HCV active agent and selected polymer can be formulated by varying the polymer concentration, the polymer to a LAP HCV active agent ratio in the solvent so as to control the gel forming rate after administration and the subsequent drug diffusion rate. The solution finally is subjected to a terminal sterilization by γ-irradiation on dry ice at a minimum dose of 25 kGy.

An example of a combination of polymers includes a polysorbate, for example, polysorbate 80 as wetting agent and a polyvinylpyrrolidone (PVP), for example, Plasdone K29/32 as a stabilizer. Therefore, in one embodiment, the present invention features a parenteral pharmaceutical composition comprising a LAP HCV active agent, or a pharmaceutically acceptable salt thereof, and polysorbate 80 and the polyvinylpyrrolidone: Plasdone K29/32.

An embodiment of the present invention is a pharmaceutical composition for parenteral administration comprising a LAP HCV active agent and a surfactant system suitable for commonly known sterilization technologies such as gamma irradiation, electron beam irradiation and autoclave sterilization.

An embodiment of the present invention is a pharmaceutical composition for parenteral administration comprising a LAP HCV active agent and a surfactant system that can be manufactured using aseptic technique.

An embodiment of the present invention is a pharmaceutical composition for parenteral administration comprising a LAP HCV active agent and a surfactant system suitable for gamma radiation sterilization.

An embodiment of the present invention is a pharmaceutical composition for parenteral administration comprising a LAP HCV active agent and a surfactant system suitable for sterilization technologies by electron beam irradiation or autoclave sterilization.

An embodiment of the present invention is a pharmaceutical composition for parenteral administration that can be presented as a "ready to use" sterile suspension or lyophile for reconstitution.

The compositions of the present invention may be administered by subcutaneous or intramuscular injection. The compositions of the present invention may also be administered by intradermal or intravitreal injection or implant. The compositions of the present invention may also be administered by other parenteral routes of administration.

The preparation of the compositions of the present invention may be performed by milling using a wet bead mill and sterilized by gamma irradiation.

Another feature of the present invention is to simplify treatment regimens and provide cure regimens for HCV with the goal of enhancing patient compliance by providing a simplified dosage form containing therapeutically effective amounts of a LAP HCV active agent or a pharmaceutically acceptable salt thereof, alone or in combination with any of the compounds of Formula IIA or IIB. Combination can mean one or more (e.g., 1, 2, or 1-2, etc) separate injections of the LAP compositions comprising a LAP HCV active agent and one more (e.g., 1, 2, or 1-2, etc) separate injections of any of the compounds of Formulas IIA or IIB. Such separate injections can be administered simultaneously, or close in time, or distant apart in time.

The present invention also features a method for treating or curing HCV infections in a human, which method comprises administering to said human any of the compositions according to the inventions described herein. The present invention features the use of a pharmaceutical composition according to the invention in the treatment or cure of HCV infections. The present invention features the manufacture of a medicament(s) according to the invention for use in medical therapy. The present invention features the manufacture of a medicament(s) according to the invention for use in the treatment or cure of HCV infection.

The present invention also features a method for treating or curing HCV infections in a human which method comprises administering to said human a composition according to the invention before, during, or after therapy with a LAP HCV active agent in tablet or solution or injectable form.

It will be appreciated by those skilled in the art that reference herein to "treatment" or "treating" or "treat" extends to the treatment of an established malady, infection or symptoms thereof. It will also be appreciated by those skilled in the art that reference herein to "cure" or "curing" extends to a patient having a complete recovery from an established malady, infection or symptoms thereof.

The present invention also features a method for preventing HCV infections in a human, which method comprises administering to said human a composition according to the invention. The present invention features the use of a pharmaceutical composition according to the invention in the prevention of HCV infections. The present invention features the manufacture of a medicament according to the invention for use in prophylactic medical therapy. The present invention features the manufacture of a medicament according to the invention for use in preventing HCV infection.

The present invention also features a method for treating or preventing HCV infections in a human which method comprises administering to said human a composition according to the invention before, during, or after therapy with a LAP HCV active agent in tablet or solution form.

Therefore, in certain embodiments of the present invention, there is provided a single treatment pharmaceutical composition comprising a therapeutically effective amount of a long acting formulation comprising a LAP HCV active agent or a pharmaceutically acceptable salt thereof, in a pharmaceutically acceptable carrier for parenteral administration.

In other embodiments, there is provided a pharmaceutical composition comprising a LAP HCV active agent that is formulated for subcutaneous administration.

In other embodiments, there is provided a pharmaceutical composition comprising a LAP HCV active agent that is formulated for intramuscular administration.

In other embodiments, there is provided a pharmaceutical composition comprising a LAP HCV active agent that is formulated for administration once weekly or longer.

In other embodiments, there is provided a pharmaceutical composition comprising a LAP HCV active agent that is formulated for administration once weekly.

In other embodiments, there is provided a pharmaceutical composition comprising a LAP HCV active agent that is formulated for administration once per month.

In other embodiments, there is provided a pharmaceutical composition comprising a LAP HCV active agent that is formulated for administration once every two months. In other embodiments, there is provided a pharmaceutical composition comprising a LAP HCV active agent that is formulated for administration once every three months. In other embodiments, there is provided a pharmaceutical composition comprising a LAP HCV active agent that is formulated for administration at any interval between 30 and 365 days.

In other embodiments, there is provided a pharmaceutical composition comprising a LAP HCV active agent, wherein the LAP HCV active agent is present in the composition in the form of crystalline nanoparticles.

In other embodiments, there is provided a pharmaceutical composition comprising a LAP HCV active agent, wherein the LAP HCV active agent is present in the composition in the form of matrix release particles.

In other embodiments, there is provided a pharmaceutical composition comprising a LAP HCV active agent, wherein the composition can be terminally sterilized by gamma irradiation.

In other embodiments, there is provided a method for the treatment of an HCV infection in a human having an HCV infection comprising administering to the human a single treatment pharmaceutical composition comprising a therapeutically effective amount of a long acting formulation comprising a LAP HCV active agent, or a pharmaceutically acceptable salt thereof, in a pharmaceutically acceptable carrier for parenteral administration.

In other embodiments, there is provided a method for the prevention of an HCV infection in a human comprising administering to a human at risk of acquiring an HCV infection, a single treatment pharmaceutical composition comprising a therapeutically effective amount of a long acting formulation comprising a LAP HCV active agent or a pharmaceutically acceptable salt thereof, in a pharmaceutically acceptable carrier for parenteral administration.

In other embodiments, there is provided a LAP pharmaceutical composition, comprising: at least one LAP HCV active agent or a pharmaceutically acceptable salt thereof.

In other embodiments, there is provided a method for the treatment of an HCV infection in a human having an HCV infection, comprising: administering to the human a LAP pharmaceutical composition including at least one LAP HCV active agent or a pharmaceutically acceptable salt thereof, in combination with a compound of Formula IIA or IIB.

In other embodiments, there is provided a method for the cure of an HCV infection in a human having an HCV infection, comprising: administering to the human a LAP pharmaceutical composition including a LAP HCV active agent or a pharmaceutically acceptable salt thereof, in combination with a compound of Formula IIA or IIB.

In other embodiments, there is provided a method for the prevention of a HCV infection in a human having an HCV infection, comprising: administering to the human a LAP pharmaceutical composition including at least one LAP HCV active agent or a pharmaceutically acceptable salt thereof, in combination with a compound of Formula IIA or IIB.

In other embodiments, there is provided a LAP pharmaceutical composition, comprising: a LAP HCV active agent, or a pharmaceutically acceptable salt thereof, further comprising a surfactant system.

In other embodiments, there is provided a LAP pharmaceutical composition, comprising: a LAP HCV active agent, or a pharmaceutically acceptable salt thereof, further comprising a surfactant system, wherein the surfactant system comprises a surfactant in an amount ranging from about 0.1% (w/v) to about 3% (w/v) surfactant, or an amount ranging from 0.2% (w/v) to about 0.4% (w/v) surfactant, or the surfactant system comprises about 0.4% (w/v) surfactant.

For purposes of the present invention, a "LAP HCV active agent" includes any conventional HCV treatment agent whether in development or approved for sale as long as it is formulated in such a way as to allow for one, two, or one to two administrations in order to achieve a a treatment induced cure. Such administrations may consist of oral administration or parenteral administration to a human having an HCV infection.

By way of example only, some suitable LAP HCV active agents may include one or more agents selected from the group consisting of Telaprevir (Incivek®), Boceprevir (Victrelis®), ABT-450, Faldaprevir (BI-201335), Asunaprevir (BMS-650032), GS-9256, GS-9857, ABT-493, Vedroprevir (GS-9451), Danoprevir (ITMN-191, RG7227), (Grazoprevir) MK-5172, Vaniprevir (MK-7009), Sovaprevir (ACH-1625), Deldeprevir (Neceprevir) (ACH-2684), Narlaprevir (SCH 900518), Simeprevir (TMC 435), ABT-267, ABT-530, Daclatasvir, Velpatasvir, Ledipasvir, ACH-2928, odalasvir (ACH-3102), PPI-668, AZD-7295, Elbasvir (MK-8742), MK-8408, BMS-986094, MK-3862 (IDX-21437), Sofosbuvir, AL-335, GS-0938, Mericitabine, BCX-5191, IDX-184, ALS-2200 (VX-135), ALS-2158, TMC649128, VX-222, ABT-072, ABT-333, Deleobuvir (BI-207127), Tegobuvir (GS-9190), Setrobuvir (ANA-598), CC-31244, Filibuvir (PF-868554), VCH-916, VCH-759, BMS-791325, TMC-647055, TKM-HCV, or a pharmaceutically salt thereof.

In other embodiments, there is provided a LAP pharmaceutical composition, comprising: a LAP HCV active agent selected from the group consisting of Telaprevir (Incivek®), Boceprevir (Victrelis®), ABT-450, Faldaprevir (BI-201335), Asunaprevir (BMS-650032), GS-9256, GS-9857, ABT-493, Vedroprevir (GS-9451), Danoprevir (ITMN-191, RG7227), (Grazoprevir) MK-5172, Vaniprevir (MK-7009), Sovaprevir (ACH-1625), Deldeprevir (Neceprevir) (ACH-2684), Narlaprevir (SCH 900518), Simeprevir (TMC 435), ABT-267, ABT-530, Daclatasvir, Velpatasvir, Ledipasvir, ACH-2928, odalasvir (ACH-3102), PPI-668, AZD-7295, Elbasvir (MK-8742), MK-8408, BMS-986094, MK-3862 (IDX-21437), Sofosbuvir, AL-335, GS-0938, Mericitabine, BCX-5191, IDX-184, ALS-2200 (VX-135), ALS-2158, TMC649128, VX-222, ABT-072, ABT-333, Deleobuvir (BI-207127), Tegobuvir (GS-9190), Setrobuvir (ANA-598), CC-31244, Filibuvir (PF-868554), VCH-916, VCH-759, BMS-791325, TMC-647055, TKM-HCV, or a pharmaceutically salt thereof.

In other embodiments, there is provided a method for the treatment (or treatment to achieve a cure) of an HCV infection in a human having an HCV infection, comprising: administering to the human a LAP pharmaceutical composition including a LAP HCV active agent, or a pharmaceutically acceptable salt thereof,
in combination with one or more additional compounds selected from the group consisting of Telaprevir (Incivek®), Boceprevir (Victrelis®), ABT-450, Faldaprevir (BI-201335), Asunaprevir (BMS-650032), GS-9256, GS-9857, ABT-493, Vedroprevir (GS-9451), Danoprevir (ITMN-191, RG7227), (Grazoprevir) MK-5172, Vaniprevir (MK-7009), Sovaprevir (ACH-1625), Deldeprevir (Neceprevir) (ACH-2684), Narlaprevir (SCH 900518), Simeprevir (TMC 435), ABT-267, ABT-530, Daclatasvir, Velpatasvir, Ledipasvir, ACH-2928, odalasvir (ACH-3102), PPI-668, AZD-7295, Elbasvir (MK-8742), MK-8408, BMS-986094, MK-3862 (IDX-21437), Sofosbuvir, AL-335, GS-0938, Mericitabine, BCX-5191, IDX-184, ALS-2200 (VX-135), ALS-2158, TMC649128, VX-222, ABT-072, ABT-333, Deleobuvir (BI-207127), Tegobuvir (GS-9190), Setrobuvir (ANA-598), CC-31244, Filibuvir (PF-868554), VCH-916, VCH-759, BMS-791325, TMC-647055, RG-101N, RG-101, anti-miR-122 oligonucleotide, any for the compounds of Formula IIA or IIB described herein, TKM-HCV, or a pharmaceutically salt thereof.

In other embodiments, there is provided a LAP pharmaceutical composition, comprising: a LAP HCV active agent, or a pharmaceutically acceptable salt thereof, in combination with any boosting agent, such as, ritonavir. The boosting agent could be dosed simultaneously as a LAP HCV active agent in the same IV or SC syringe, or it could be dosed separately as an oral tablet or capsule.

The pharmaceutical compositions of the invention are presented as pharmaceutical compositions suitable for parenteral administration. The compositions may also include a safe and effective amount of other active ingredients, such as antimicrobial agents, antiviral agents, or preservatives.

It will be appreciated by those skilled in the art that the amount of active ingredients required for use in treatment will vary according to a variety of factors, including the nature of the condition being treated and the age and condition of the patient, and will ultimately be at the discretion of the attending physician, veterinarian or health care practitioner.

Compositions of the present invention enable patients greater freedom from multiple dosage regimens and ease the needed diligence required in remembering complex daily dosing times and schedules. The compositions of the present invention are particularly suitable for administration as a single dose, monthly, bi-monthly or tri-monthly, or at any interval between 30 and 365 days.

Advantageously, the compositions of the present invention may be administered once.

The compositions of the present invention may be used in combination with other pharmaceutical formulations as a component of a multiple drug treatment regimen. Such combinations could be administered to a subject in one dosage unit, such as a fixed dose combination or it could be administered in separate dosage units.

In one embodiment, a combination of one or more pharmaceutical formulations may be administered to a subject in separate dosage units comprising a first dosage unit of a LAP HCV active agent and a second dosage unit of a LAP HCV active agentIA or Formula IIB, administered either serially, or simultaneously. The unit dosage unit of a LAP HCV active agent and/or the unit dosage unit of a LAP HCV active agentIA or Formula IIB may be administered intravenously, topically, or by injection, or by other suitable method, in a saline solution or other pharmaceutically acceptable formulation as described herein.

Compositions of the present invention may also be packaged as articles of manufacture comprising a therapeutically effective amount of a LAP HCV active agent, or a pharmaceutically acceptable salt thereof; and therapeutically effective amount of one or more of the following: nucleoside NS5B polymerase inhibitors, non-nucleoside NS5B polymerase inhibitors, NS3/4A protease inhibitor, NS5A inhibitor and NS3 protease inhibitor. In one embodiment, the compositions of the present invention could be administered to a subject in combination with one or more of the following HCV treatment compounds: in combination with one or more additional compounds selected from the group consisting of Telaprevir (Incivek®), Boceprevir (Victrelis®), ABT-450, Faldaprevir (BI-201335), Asunaprevir (BMS-650032), GS-9256, GS-9857, ABT-493, Vedroprevir (GS-9451), Danoprevir (ITMN-191, RG7227), (Grazoprevir) MK-5172, Vaniprevir (MK-7009), Sovaprevir (ACH-1625), Deldeprevir (Neceprevir) (ACH-2684), Narlaprevir (SCH 900518), Simeprevir (TMC 435), ABT-267, ABT-530, Daclatasvir, Velpatasvir, Ledipasvir, ACH-2928, odalasvir (ACH-3102), PPI-668, AZD-7295, Elbasvir (MK-8742), MK-8408, BMS-986094, MK-3862 (IDX-21437), Sofosbuvir, AL-335, GS-0938, Mericitabine, BCX-5191, IDX-184, ALS-2200 (VX-135), ALS-2158, TMC649128, VX-222, ABT-072, ABT-333, Deleobuvir (BI-207127), Tegobuvir (GS-9190), Setrobuvir (ANA-598), CC-31244, Filibuvir (PF-868554), VCH-916, VCH-759, BMS-791325, TMC-647055, TKM-HCV, or a pharmaceutically salt thereof.

The packaging material may also have labeling and information related to the pharmaceutical composition printed thereon. Additionally, an article of manufacture may contain a brochure, report, notice, pamphlet, or leaflet containing product information. This form of pharmaceutical information is referred to in the pharmaceutical industry as a "package insert." A package insert may be attached to or included with a pharmaceutical article of manufacture. The package insert and any article of manufacture labeling provides information relating to the pharmaceutical composition. The information and labeling provides various forms of information utilized by health-care professionals and patients, describing the composition, its dosage and various other parameters required by regulatory agencies such as the United States Food and Drug Agencies.

The present invention further provides the following embodiments:
(a) A parenteral pharmaceutical composition comprising an effective amount of LAP HCV active agent or a pharmaceutically acceptable salt thereof, for the cure of HCV infection, or prevention of HCV infection in an individual at risk of being infected by HCV, wherein the composition is administered as a single treatment
(b) The composition according to (a) wherein the composition is administered once every two weeks.
(c) The composition according to (a) wherein the composition is administered once every month.
(d) The composition according to any one of (a) to (c) wherein the effective amount of LAP HCV active agent or a pharmaceutically acceptable salt thereof is selected such that the blood plasma concentration of LAP HCV active agent in a subject is kept during a prolonged period of time at a level between a maximum blood plasma level which is the blood plasma level that causes significant side effects and the minimum blood plasma level that is the lowest blood plasma level that causes a LAP HCV active agent to provide effective treatment or prevention of HCV infection.
(e) The composition according to (d) wherein the blood plasma level of a subject is kept at a level equal to or above about 150 ng/ml, in particular equal to or above about 600 ng/ml.
(f) The composition according to any one of (a) to (e), wherein the composition is administered subcutaneously or intramuscularly.
(g) The composition according to any one of (a) to (f), which comprises the aforementioned surfactant system comprising polysorbate and/or polyvinylpyrrolidone.
(h) A method for the treatment or prevention of an HCV infection in a human comprising a pharmaceutical composition according to any of the above (a) to (g).

The dose of a LAP HCV active agent administered, which is the amount of the LAP HCV active agent in the parenteral composition for use in the invention, may be selected such that the blood plasma concentration of the LAP HCV active agent in a subject is kept during a prolonged period of time above a minimum blood plasma level. The term "minimum blood plasma level" (or $C_{min}$) in this context refers to the lowest efficacious blood plasma level, that is, the blood plasma level of the compound of formula (I) that provides effective prevention or treatment HCV infection. In the case of transmission of HCV from an individual infected by HCV to an individual not infected by HCV, this is the lowest blood plasma level that is effective in inhibiting said transmission.

The blood plasma level of the LAP HCV active agent in a subject may be kept at a level above a minimum blood plasma level of about 170 ng/ml, about 700 ng/ml, or about 1000 ng/ml. The blood plasma levels of the compound of formula (I) in a subject may be kept above these minimum blood plasma levels because at lower levels the drug may no longer be effective, thereby increasing the risk of transmission of HCV infection, and may be suboptimal for treatment of HCV infected subjects. Plasma levels of the LAP HCV active agent may be kept at higher levels to avoid the development of HCV mutations, while maintaining a safety margin.

An advantage of the mode of administration of the LAP HCV active agent is that high $C_{min}$ levels can be achieved without a commensurate high $C_{max}$, which could mitigate potential side effects associated with $C_{max}$.

The effective amount of an HCV active agent to be administered may be selected such that the blood plasma concentrations in a subject (or patient) are kept during a prolonged period of time at a level between a maximum plasma level (or $C_{max}$) and the minimum blood plasma level (or $C_{min}$).

In some embodiments the blood plasma level of an HCV active agent in a subject may be kept between the minimum blood plasma level (or $C_{min}$ as specified above) and the lower maximum plasma level of an HCV active agent (or $C_{max}$) which is defined as the level that corresponds to the lowest blood plasma level where an HCV active agent acts therapeutically. The lowest level where an HCV active agent acts therapeutically is the lowest blood plasma level that is effective in inhibiting replication of HCV in individuals infected by HCV so that the viral load of HCV is relatively low, for example where the viral load (represented as the number of copies of viral RNA in a specified volume of serum) is below about 200 copies/ml, in particular below about 100 copies/ml, more particularly below 50 copies/ml, specifically below the detection limit of the assay for HCV.

As mentioned above, the blood plasma levels of an HCV active agent depend on the amount of active ingredient in each parenteral dosage administered. However, it also depends on the frequency of the administrations (i.e. the time interval between each administration). Both parameters can be used to direct the blood plasma levels to the desired values. The dose may be higher where administrations are less frequent or a single treatment represents the course of therapy.

Although the plasma levels of an HCV active agent should remain below a maximum or above a minimum value, they may surpass the maximal value or drop below the minimal value during relatively short periods of time, which is usually kept as short as possible. The maximum and minimum plasma levels therefore can be expressed as mean plasma levels during a certain period of time.

In some instances there may be a small initial plasma concentration peak shortly after administration, after which the plasma levels achieve a steady-state.

The compositions of the present invention conveniently allow administration of a LAP HCV active agent in unit dosage form containing, for example, from about 1 mg to about 1000 mg, from about 20 mg to about 100 mg, from about 20 mg to about 300 mg, from about 25 mg to about 800 mg, from about 25 mg to about 100 mg, from about 100 mg to about 200 mg, from about 200 mg to about 400 mg, from about 100 mg to about 800 mg, from about 100 mg to about 600 mg, from about 100 mg to about 400 mg per unit dosage form, or from about 400 mg to about 800 mg. In one embodiment, the unit dose is from about 400 mg to about 800 mg, which is administered to the subject once. In another embodiment, the subject could be dosed once with 800 mg which may be split into multiple sequential injections.

The unit dose concentration of a LAP HCV active agent in the formulation may be selected from any of the following ranges: 5-25 mg/mL, 25-50 mg/mL, 50-150 mg/mL, or 150-300 mg/mL.

Once administered, the blood plasma levels of an HCV active agent in a subject may be more or less stable. After initial rise of the blood plasma levels, a steady state mode may be achieved during a prolonged period of time. By "steady state" is meant the condition in which the amount of drug present in the blood plasma of a subject stays at more or less the same level over a prolonged period of time. The plasma levels of an HCV active agent may then gradually decrease over time, and when the minimum plasma level is reached, then the next dose of an HCV active agent may be administered. Alternatively, the virus may be cleared through a single treatment intervention. The term "stays at more or less the same level" does not exclude that there can be small fluctuations of the plasma concentrations within an acceptable range, for example, within about 30%, about 20%, or about 10%.

The parenteral compositions of an HCV active agent may be administered by intravenous injection or, preferably by subcutaneous or intramuscular administration.

The present invention is based on the use of parenteral compositions of the HCV active agent and therefore the nature of the carrier is selected for suitability for parenteral administration. The carrier in most cases will comprise sterile water, in although other ingredients, for example, to aid solubility, may be included. Injectable solutions or suspensions, for example, may be prepared in which the carrier comprises saline solution, glucose solution or a mixture of saline and glucose solution. Further, the carrier may contain the surfactant system mentioned above such as polysorbate and Poloxamers.

The parenteral pharmaceutical composition comprising an HCV active agent of the present invention is long-acting. Accordingly, the composition is useful for the treatment or prevention of HCV infection with administration at long time intervals, compared with conventional compositions or with other compounds similar to an HCV active agent in chemical structure. The compositions of the present invention can be administered to a patient once or intermittently, e.g., once per week, once per month, once per every 2 months, or one per every 3 months. In one embodiment, the compositions of the present invention could be administered at higher dosages (e.g., 800 mg) as a "loading dose" for the first one to three months, while after the first one to months the dosage could be lowered.

Therefore, the compositions of the present invention and an administration by subcutaneous (SC) or intramuscular (IM) injection using the same can lead to a remarkable reduction or elimination of medication (pill) burden and difficulty in patient compliance. Further, such intermittent administration of a composition of the present invention can contribute to maintaining therapy at appropriate compliance which leads to prevention of emergence of drug resistant HCV while the virus is cleared.

In embodiment, a LAP HCV active agent formulation is a liquid suspension form for a bolus intramuscular or subcutaneous administration at a concentration ranges from 10 mg/ml to 250 mg/ml and having an injection volume of up to 4 ml (e.g., 2 injections, each 2 ml).

In some embodiments, the LAP pharmaceutical composition comprising a LAP HCV active agent further comprises, a surfactant system.

In some embodiments, the LAP pharmaceutical composition comprising a LAP HCV active agent further comprises a surfactant in an amount ranging from about 0.1% (w/v) to about 10% (w/v) surfactant.

In some embodiments, the LAP pharmaceutical composition comprising a LAP HCV active agent further comprises a surfactant in an amount ranging from about 1% (w/v) to about 8% (w/v) surfactant.

In some embodiments, the LAP pharmaceutical composition comprising a LAP HCV active agent further comprises about 2% (w/v) surfactant.

In some embodiments, the LAP pharmaceutical composition comprising a LAP HCV active agent further comprises a surfactant selected from the group consisting of polyoxyethylene sorbitan fatty acid esters, poloxamers, sorbitan esters of fatty acids (SPAN), polyethoxylated castor oil and its derivatives, tocopheryl polyethylene glycol succinate, and polyvinyl alcohols.

In some embodiments, the LAP pharmaceutical composition comprising a LAP HCV active agent further comprises a surfactant that is polysorbate 20.

In some embodiments, the LAP pharmaceutical composition comprising a LAP HCV active agent further comprises a surfactant system which comprises a stabilizer that is selected from the group consisting of polyethylene glycols, carboxymethylcellulose calcium, carboxymethylcellulose sodium, methylcellulose, hydroxyethylcellulose, hydroxypropylcellulose, hydroxymethylpropylcellulose, polysaccharides, hyarluronic acid, polyvinyl alcohol (PVA) and polyvinylpyrrolidone (PVP).

In some embodiments, the LAP pharmaceutical composition comprising a LAP HCV active agent further comprises a surfactant system comprises a stabilizer that is polyethylene glycol.

In some embodiments, the LAP pharmaceutical composition comprising a LAP HCV active agent further comprises a surfactant system comprises a stabilizer that is PEG-3350.

In some embodiments, the LAP pharmaceutical composition comprising a LAP HCV active agent further comprises a surfactant system which comprises a stabilizer in an amount that ranges from about 1% (w/v) to about 5% (w/v) stabilizer.

In some embodiments, the LAP pharmaceutical composition comprising a LAP HCV active agent further comprises a surfactant system which comprises about 2% (w/v) stabilizer.

In some embodiments, the LAP pharmaceutical composition comprising a LAP HCV active agent further comprises a surfactant system which comprises a buffer salt.

In some embodiments, the LAP pharmaceutical composition comprising a LAP HCV active agent further comprises a surfactant system which comprises a buffer salt that is acetate buffered saline.

In some embodiments, the LAP pharmaceutical composition comprising a LAP HCV active agent further comprises a surfactant system which comprises a buffer salt at a concentration of about 10 mM.

In some embodiments, the LAP pharmaceutical composition comprising a LAP HCV active agent where a LAP HCV active agent is in a crystalline form prior to encapsulating into a microparticle and combining with a surfactant system.

In some embodiments, the LAP pharmaceutical composition comprising a LAP HCV active agent, wherein a LAP HCV active agent is in a crystalline microparticle form.

In some embodiments, the LAP pharmaceutical composition comprising a LAP HCV active agent, wherein a LAP HCV active agent is in a microparticle form, wherein the microparticles of a LAP HCV active agent range in size from about 0.05 µm to about 100 µm.

In some embodiments, the LAP pharmaceutical composition comprising a LAP HCV active agent, wherein a LAP HCV active agent is in a microparticle form, wherein the microparticles of a LAP HCV active agent range in size from about 0.1 µm to about 5 µm.

In some embodiments, the LAP pharmaceutical composition comprising a LAP HCV active agent, wherein a LAP HCV active agent is encapsulated in a polymer.

In some embodiments, the LAP pharmaceutical composition comprising a LAP HCV active agent, wherein a LAP HCV active agent is encapsulated in a polymer that comprises poly (lactic-co-glycolic) acid.

In some embodiments, the human having an HCV infection is administered the LAP pharmaceutical composition including a LAP HCV active agent, on a dosing regimen ranging from about every week to about every three months.

In some embodiments, the human having an HCV infection is administered the LAP pharmaceutical composition including a LAP HCV active agent, on a dosing regimen ranging from about every week to about every two months.

In some embodiments, the human having an HCV infection is administered the LAP pharmaceutical composition including a LAP HCV active agent, on a dosing regimen that is monthly.

In some embodiments, the human having an HCV infection is administered the LAP pharmaceutical composition including a LAP HCV active agent on a dosing regimen that is only one administration.

In some embodiments, the human having an HCV infection is administered the LAP pharmaceutical composition including a LAP HCV active agent on a dosing regimen that is only one administration comprising 1 or 2 injections.

In some embodiments, the LAP pharmaceutical composition comprising a LAP HCV active agent, where a LAP HCV active agent is in a microparticle form, wherein the microparticles of a LAP HCV active agent range in size from about 0.05 µm to about 100 µm, wherein said microparticles comprise substantially the same size.

In some embodiments, the LAP pharmaceutical composition comprising a LAP HCV active agent, where a LAP HCV active agent is in a microparticle form, wherein the microparticles of a LAP HCV active agent range in size from about 0.05 µm to about 100 µm, wherein said microparticles comprise two or more substantially different particle sizes that provide for earlier and later release after administration to a subject and result in varying absorption kinetics therein.

In some embodiments, the LAP pharmaceutical composition comprising a LAP HCV active agent, wherein a LAP HCV active agent is in a microparticle form, wherein the microparticles of a LAP HCV active agent range in size from about 0.05 µm to about 0.5 µm.

In some embodiments, the LAP pharmaceutical composition comprising a LAP HCV active agent, where a LAP HCV active agent is in a microparticle form, wherein the microparticles of a LAP HCV active agent range in size from about 0.5 µm to about 5 µm.

In some embodiments, the LAP pharmaceutical composition comprising a LAP HCV active agent, where a LAP HCV active agent is in a microparticle form, wherein the microparticles of a LAP HCV active agent range in size from about 5 µm to about 25 µm.

In some embodiments, the LAP pharmaceutical composition comprising a LAP HCV active agent, where a LAP HCV active agent is in a microparticle form, wherein the microparticles of a LAP HCV active agent range in size from about 25 µm to about 100 µm.

In some embodiments, the LAP pharmaceutical composition comprising a LAP HCV active agent, where a LAP HCV active agent is present in an amount ranging from about 20 mg to about 100 mg.

In some embodiments, the LAP pharmaceutical composition comprising a LAP HCV active agent, wherein a LAP HCV active agent is present in an amount ranging from about 100 mg to about 200 mg.

In some embodiments, the LAP pharmaceutical composition comprising a LAP HCV active agent, wherein a LAP HCV active agent is present in an amount ranging from about 200 mg to about 400 mg.

In some embodiments, the LAP pharmaceutical composition comprising a LAP HCV active agent, where a LAP HCV active agent is present in an amount ranging from about 400 mg to about 800 mg.

In other embodiments, there is provided a long acting parenteral (LAP) pharmaceutical composition comprising a LAP HCV active agent, or a pharmaceutically acceptable salt thereof, and one or more pharmaceutically acceptable excipients that comprise:
a) Poloxamer 188;
b) PEG3350;
c) D-mannitol;
d) a buffer comprising sodium acetate or sodium phosphate or both; and
e) water.

In other embodiments, there is provided a long acting parenteral (LAP) pharmaceutical composition comprising a LAP HCV active agent, or a pharmaceutically acceptable salt thereof, wherein a LAP HCV active agent is present at a concentration that ranges from 100-150 mg/ml, and one or more pharmaceutically acceptable excipients that comprise:

| Component | Function | Concentration (mg/ml) |
|---|---|---|
| Poloxamer 188 | Wetting agent | 50 |
| PEG3350 | Stabilizer | 20 |
| Mannitol | Tonicity agent | 45 |
| Sodium acetate or sodium phosphate | Buffer | 20 mM |
| Water | Solvent | Q.S. |

In other embodiments, there is provided a method for curing an HCV infection in a human having an HCV infection, comprising: administering to the human the above LAP pharmaceutical composition.

In other embodiments, there is provided a method of curing an HCV infection in a human comprising administering to the human any of the above LAP pharmaceutical compositions comprising a LAP HCV active agent, wherein the administration comprises 1-2 injections of the LAP pharmaceutical composition.

In other embodiments, there is provided the method above wherein the administration comprises 1 intramuscular injection of the LAP pharmaceutical composition.

In other embodiments, there is provided a kit comprising a stoppered glass vial comprising a long acting parenteral (LAP) pharmaceutical composition comprising a LAP HCV active agent, or a pharmaceutically acceptable salt thereof, and one or more pharmaceutically acceptable excipients that comprise:
a) Poloxamer 188;
b) PEG3350;
c) D-mannitol;
d) a buffer comprising sodium acetate or sodium phosphate or both; and
e) water.

In other embodiments, there is provided a LAP pharmaceutical composition, comprising: a LAP HCV active agent, or a pharmaceutically acceptable salt thereof, further comprising a surfactant system.

Also provided in the present invention are compounds of Formula IIA and IIB, which are anti-microRNA compounds that are complementary to microRNA 122 (miR122) and are known as anti-miR122 compounds or anti-mi-122 oligonucleotides.

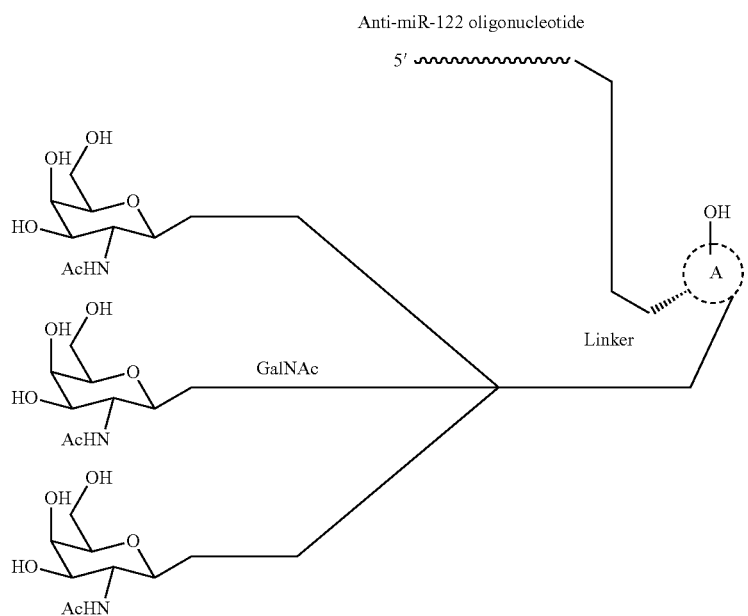

IIA

Anti-miR-122 oligonucleotide

-continued

IIB

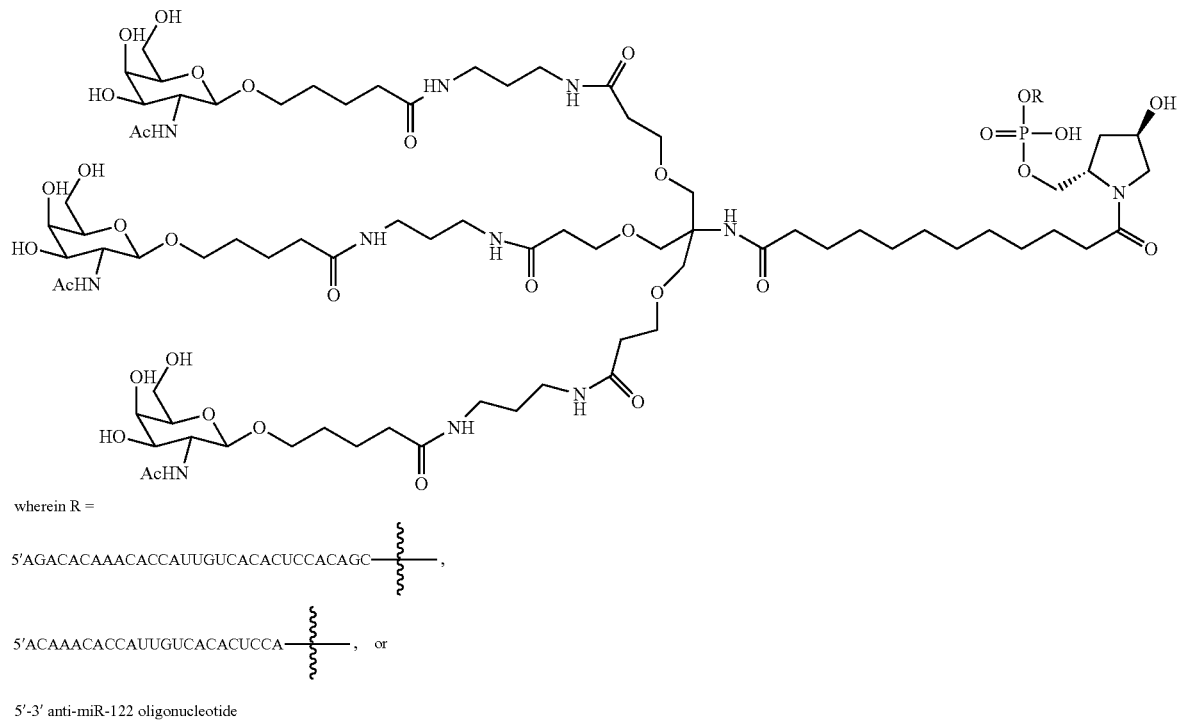

wherein R =

5′AGACACAAACACCAUUGUCACACUCCACAGC—§—,

5′ACAAACACCAUUGUCACACUCCA—§—, or

5′-3′ anti-miR-122 oligonucleotide

Compounds of Formula IIA or IIB may be used, in combination with a LAP HCV active agent, in the treatment, prevention, or cure of HCV. The combinations may be administered in separate formulations, at separate times; the combinations of a LAP HCV active agent and a compound of formula IIA or Formula IIB may be administered in separate formulations as separate unit dosages, and may be administered serially, simultaneously; in addition, the combinations of a LAP HCV active agent and a compound of Formula IIA or IIB may be administered in a single pharmaceutical formulation; and/or the combination may be administered in a fixed dose combination. The anti-miR-122 oligonucleotide of Formula IIA and defined by R in Formula IIB may comprise any sequence that is described in U.S. Pat. Nos. 8,217,020 and 8,759,312; EP1,747,023; and JP4,943,322, each of which is incorporated by reference herein in its entirety.

In selected compounds of Formula IIA, ring A may be independently selected from cycloalkyl or heterocyclyl.

The compounds of Formula IIA and Formula IIB may be modified. In certain embodiments, the anti-miR-122 oligonucleotide of Formula IIA or Formula IIB comprises at least one modified internucleoside linkage, modified sugar moiety, or modified nucleobase. In certain embodiments the anti-miR-122 oligonucleotide of Formula IIA or Formula IIB comprises at least one 2′-O-methoxyethyl sugar moiety. In certain embodiments the anti-miR-122 oligonucleotide of Formula IIA or Formula IIB comprises at least one phosphorothioate internucleoside linkage. In certain embodiments the anti-miR-122 oligonucleotide of Formula IIA or Formula IIB comprises at least one 5-methylcytosine. In certain embodiments the anti-miR-122 oligonucleotide of Formula IIA or Formula IIB comprises a phosphorothioate internucleoside linkage and comprises at least one 5-methylcytidines. In certain embodiments the anti-miR-122 oligonucleotide of Formula IIA or Formula IIB comprises at least one constrained ethyl moiety.

Compounds of Formula IIA and IIB may be prepared as described in U.S. Pat. Nos. 8,217,020 and 8,759,312; EP1,747,023; and JP4,943,322, and may comprise any of the sequences described therein, all of which are incorporated by reference herein in their entirety.

Discussions of RG-101 and RG-101N can be found in Nature Review Genetics: Regulation of microRNA biogenesis, function and degradation, Jacek Krol, Inga Loedige and Witold Filipowicz; October 2010 Vol 11 No. 10; and in the poster "RG-101, a GalNAc-conjugated anti-miR Employing a Unique Mechanism of Action by Targeting Host Factor MicroRNA-122 (miR-122), Demonstrates Potent Activity and Reduction of HCV in Preclinical Studies", Balkrishen Bhat, Steven Neben, Jia Tay, Kai Liu, Nelson Chau, Daniel Hogan, Deidre MacKenna, Neil Gibson, The 64th Annual Meeting of the American Association for the Study of Liver Disease, Walter E. Washington Convention Center—Washington, D.C. Nov. 1-5, 2013, all of which are incorporated by reference herein in their entirety.

Anti-miR oligonucleotides may be modified by conjugation with carbohydrates such as D-galactose, D-mannose, N-acetyl-D-galactose (GalNAc), multivalent N-acetyl-D-galactose including dimers and trimers of N-acetyl-D-galactose, multivalent lactose, multivalent galactose, N-acetyl-galactosamine, N-acetyl-gulucosamine, multivalent mannose and multivalent fucoses, using chemistry and delivery systems described in US Publications No. US20130236968 and US20110123520, the contents of which are hereby incorporated by reference herein in their entirety.

Anti-miR oligonucleotides may also be modified by modifying the sugar using known chemistries such as locked nucleic acid (LNA) chemistry and/or addition of 2'-constrained ethyl (cEt). moieties, to create constrained sugars, and/or addition of 2'-methoxyethyl moieties (2'-MOE) on the sugar. Preferred oligonucleotides comprise one of the following at the 2' position: OH; F- O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3]_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-O-methoxyethyl (2'-O—$CH_2CH_2OCH_3$, also known as 2'-O-(2-methoxyethyl) or 2'-methoxyethoxy or 2'-MOE) (Martin et al., Helv. Chim. Acta, 1995, 78, 486-504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in examples herein below, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$.

Other modifications include 2'-methoxy (2'-O—$CH_3$), 2'-aminopropoxy (2'-$OCH_2CH_2CH_2NH_2$), 2'-allyl (2'-$CH_2$—CH=$CH_2$), 2-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, each of which is herein incorporated by reference in its entirety.

A further modification of the sugar includes Locked Nucleic Acids (LNAs) in which the 2'-hydroxyl group is linked to the 3' or 4' carbon atom of the sugar ring, thereby forming a bicyclic sugar moiety. The linkage is preferably a methylene (—$CH_2$—)$_n$ group bridging the 2' oxygen atom and the 4' carbon atom wherein n is 1 or 2. LNAs and preparation thereof are described in International Patent Publication Nos. WO 98/39352 and WO 99/14226, incorporated by reference herein in their entirety.

The phosphodiester backbone may be modified by using e.g. phosphorothioate bonds, or phosphotriester bonds between the nucleotides in place of phosphodiester bonds. Preferred backbone modifications are phsophorothioate, phosphorodithioate, phosphoramidate, phosphonate, alkyl-phosphonate, siloxane, carbonate, carboxymethyl, carbamate, amide, thioether, ethylene oxide linker, sulfonate, sulfonamide, thioformacetal, formacetal, oxime, methyleneimino, methyleneaminocarbonyl, methylenem-ethylimino (MMI), methylenehydrazo, methylenedimethylhydrazo (MDH) and methyleneoxymethylimino.

In addition, the nucleobases may be modified by using modified nucleobases known in the art. Examples include: synthetic and natural nucleobases, e.g., inosine, thymine, xanthine, hypoxanthine, nubularine, isoguanisine, or tubercidine; modified analogs of any of the purine or pyrimidine known in the art, including 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and 0-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine,7-deazaadenine, N6, N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3-carboxypropyl)uracil, 3-methylcytosine, 5-methylcytosine, $N^4$-acetyl cytosine, 2-thiocytosine, N6-methyladenine, N6-isopentyladenine, 2-methylthio-N-6-isopentyladenine, N-methylguanines, or O-alkylated bases.

EXAMPLES

The following examples further describe and exemplify particular embodiments within the scope of the present Invention. The examples are given solely for illustration and are not to be construed as limitations as many variations are possible without departing from spirit and scope of the Invention.

A LAP HCV active agent, may be synthesized by one of skill in the art by following the teachings of PCT Published Application No. WO2013028371 deriving from U.S. Provisional Application 61/525,440, filed Aug. 19, 2011 which disclose a class of compounds useful in the treatment of HCV infection.

A Thermo Orion 9110DJWP microelectrode and a Metrohmn 827 pH Meter were used for pH measurements. An Advanced Micro-Osmometer 3320 was used for osmolarity measurements. A Retsch PM400 planetary mill was used for wet bead milling.

Example 1

Preparation of LAP Vehicle 1.0 g of Polysorbate 80 was added to a 0.5 L volumetric flask. About 100 mL of Water for Injection (WFI) was added to the flask to dissolve. 8.5 g of Plasdone K29/32 was added to the flask with an additional 300 mL of WFI. The contents were stirred with a stir bar to dissolve. Phosphate buffer: 0.11039 g $NaH_2PO_4$; 0.27598 g $NaH_2PO_4:H_2O$; and 0.22572 g $Na_2HPO_4$ along with 4.16389 g NaCl as isotonicity agent was added. The mixture was again stirred to dissolve and then was q.s. to 500 mL. The solution was filtered through a 0.22 micrometer Corning filter. The resultant LAP vehicle was 1.7% w/v Plasdone K29/32 and 0.2% w/v Polysorbate 80 in phosphate buffer: 0.004M $NaH_2PO_4$ and 0.006M $Na_2HPO_4$.

Example 2

Homogenized Suspension Compositions (a) 2.5 mg/ml Homogenized Solution of a LAP HCV Active Agent in LAP Vehicle for Subcutaneous Injection (SC).

17.5 mg of the LAP HCV active agent was added to a clear 10 ml sterile vial with a crimp cap. The LAP Vehicle (as prepared in Example 1) was added to a weight of 7 grams. The solution was homogenized using a handheld Polytron PT1200F homogenizer for 1-2 minutes with a speed increasing from low to near max. The solution was then stirred at ambient room temperature. The resulting title solution had an osmolarity of 313 mOsm/kg and pH of 5.49. The solution was utilized for 5 mg/kg SC injections.

(b) 10.0 mg/ml Homogenized Solution of a LAP HCV Active Agent in LAP Vehicle for SC and IM (Intra-muscular) Injection 40 mg of the LAP HCV active agent was added to a clear 10 ml sterile vial with a crimp cap. The LAP Vehicle (as prepared in Example 1) was added to a weight of 4 grams. The solution was homogenized using a handheld Polytron PT1200F homogenizer for 1-2 minutes with a speed increasing from low to near max. The solution was then stirred at ambient room temperature. The resulting title solution had an osmolarity of 330 mOsm/kg and pH of 5.47. The solution was utilized for 5 mg/kg IM injections.

Example 3

Wet Bead Milling Formulations (a) Preparation of Wet Bead Milled Stock Suspension of a LAP HCV Active Agent in LAP Vehicle 1000 mg of a LAP HCV active agent is weighed into a 50 mL milling vessel. compound of Formula I was added to a clear 10 ml sterile vial with a crimp cap. The LAP Vehicle (as prepared in Example 1) was added to a weight of 10 grams thereby yielding a 100 mg/ml suspension. Beads were added at 4× suspension volume and the milling vessel was sealed with security tape. Milling was started at 250 rpm for 2 hours using a planetary mill PM400 with a 15 minute interval. After 2 hours the milling vessel was left in the planetary mill for 1.5 hours at ambient room temperature. The beads were filtered using a 25 mm Easy pressure Syringe Filter Holder (screen size:149 micrometers). A milky suspension was collected and stirred with a stir bar to defoam. The resulting wet bead milled (WBM) suspension had an osmolarity of 303 mOsm/kg and pH of 7.2. The solution was utilized for preparing the WBM suspensions following.

(b) 10.0 mg/ml WBM Suspension of a LAP HCV Active Agent in LAP Vehicle for IM Injection 0.294 g of WBM suspension of Example 3(a) was added to a clear 5 ml sterile vial with a crimp cap. The LAP Vehicle (as prepared in Example 1) was added to a weight of 3 grams. The contents were swirled to mix. The resulting title solution had a pH of 5.28. The solution was utilized for 5 mg/kg IM injections.

(c) 2.5 mg/ml WBM Suspension of a LAP HCV Active Agent in LAP Vehicle for SC Injection 0.122 g of WBM suspension of Example 3(a) was added to a clear 5 ml sterile vial with a crimp cap. The LAP Vehicle (as prepared in Example 1) was added to a weight of 5 grams. The contents were swirled to mix. The resulting title solution had a pH of 5.57. The solution was utilized for 5 mg/kg SC injections.

Injections were made in Sprague-Dawley rats SC and IM at 5 mg/kg doses with $T_{1/2}$, $C_{max}$, $T_{max}$, and AUC being measured. Results are shown in Table 1 and FIG. 1.

TABLE 1

| Route of Administration | Formulation | Dose | $T_{1/2}$ (days) | $C_{max}$ (ng/ml) | $T_{max}$ (h) | $AUC_{last}$(h*µg/ml) |
|---|---|---|---|---|---|---|
| SC | WBM | 5 | 2.7 | 327.3 ± 58.3 | 6.7 ± 1.2 | 10.36 ± 2.1 |
| | Homogenized suspension | 5 | 12 | 130 ± 17.6 | 6.7 ± 2.3 | 6.4 ± 1.0 |
| IM | WBM | 5 | 5 | 293 ± 110.4 | 5.3 ± 1.2 | 9.95 ± 2.9 |
| | Homogenized suspension | 5 | 8 | 155.7 ± 15.0 | 5.3 ± 1.2 | 6.28 ± 0.74 |

Example 4

Determination of the Pharmacokinetics of Compound of Formula I in Two Formulations after a Single Intramuscular Administration to Dogs (n=3 Per Group)

Dose Administration: Individual doses were calculated based on body weights recorded on the day of dose administration. Animals were given an intramuscular (IM) injection. The number of injection sites was based upon dose volume and was recorded in the data. The IM injection sites were monitored and any unusual observations noted throughout the duration of the study and recorded in the raw data.

Sample Collection, Handling, Storage, and Shipment: Blood was collected into tubes containing $K_2$EDTA anticoagulant. Blood (approximately 1 mL) was collected from each animal predose and at 0.5, 1, 2, 4, 8, 24, 48, 72, 96, 120, 144, 168, 192, 264, 336, 432, 504, 600, 672, 768, 840, 936, 1008, 1104, 1176, 1272, 1344, 1440, 1512, 1608, and 1680 hours post test article dose. Blood was collected via a jugular vein. Another vein may have been used as an alternative blood collection site and the site recorded in the data.

Sample Handling and Storage: Blood for pharmacokinetics was maintained on wet ice or at approximately 4° C. prior to centrifugation to obtain plasma. Centrifugation began within 1 hour of collection. Plasma was acidified by mixing with an equal volume of 50 mM (in water) citrate buffer (pH ~4.0). For each sample, all plasma (up to tube volume) was placed into 96-well plate with individual tubes for each and stored at <−60° C. until shipment. Tubes were arranged by time point by group/row with time points from left to right.

Sample Analysis: Plasma samples were analyzed for concentrations of a LAP HCV active agent by bioanalytical services using a liquid chromatography/mass spectrometry (LC-MS/MS) method.

Pharmacokinetic Analysis: Pharmacokinetic analyses included determination of maximum concentration ($C_{max}$), time to maximum concentration ($T_{max}$), total area under the curve (AUC), and half-life ($t_{1/2}$).

TABLE 2

| Component | Function | Concentration (mg/ml) |
| --- | --- | --- |
| Compound of Formula I | Active | 50-250 |
| Poloxamer 188, or Tween 20, or Tween 80 | Wetting agent | 20-120 |
| PEG3350 | Stabilizer | 20 |
| Mannitol | Tonicity agent | 30-45 |
| Sodium acetate or sodium phosphate | Buffer | 0-20 mM |

FIG. 2 represents individual concentration—time plots from dogs administered a micronized suspension of compound of formula I formulated with Poloxamer 188 as the wetting agent at a dose level of 100 mg/kg. FIG. 3 represents individual concentration—time plots from dogs administered a nanomilled suspension of compound of formula I formulated with Poloxamer 188 as the wetting agent at a dose level of 100 mg/kg. FIG. 4 represents individual concentration—time plots from dogs administered a micronized suspension of compound of formula I formulated with Tween 20 as the wetting agent at a dose level of 10 mg/kg. FIG. 5 represents individual concentration—time plots from dogs administered a nanomilled suspension of compound of formula I formulated with Tween 80 as the wetting agent at a dose level of 10 mg/kg.

What is claimed is:

1. A method for the treatment of an HCV infection in a human having an HCV infection, comprising:

administering to the human a long acting parenteral (LAP) pharmaceutical composition comprising a LAP HCV active agent, or a pharmaceutically acceptable salt thereof, wherein the LAP HCV agent is 6-(N-(7-chloro-1-hydroxy-1,3-dihydrobenzo[c][1,2]oxaborol-5-yl)methylsulfonamido)-5-cyclopropyl-2-(4-fluorophenyl)-N-methylbenzofuran-3-carboxamide, in combination with a compound of Formula IIA or IIB:

IIA

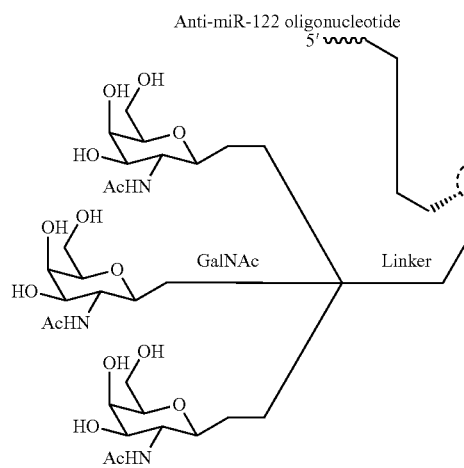

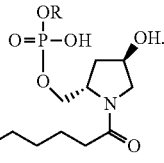

wherein ring A may be independently selected from cycloalkyl or heteroaryl wherein R =

5'AGACACAAACACCAUUGUCACACUCCACAGC—{, SEQ ID NO. 1

5'ACAAACACCAUUGUCACACUCCA—{, or SEQ ID NO. 2

5'-3' anti-miR-122 oligonucleotide-,

2. The method according to claim 1, wherein R is a 5'-3' anti-miR-122 oligonucleotide and wherein the anti-miR-122 oligonucleotide comprises at least one modified internucleoside linkage, modified sugar moiety, or modified nucleobase.

3. The method according to claim 1, wherein R is a 5'-3' anti-miR-122 oligonucleotide and wherein the anti-miR-122 oligonucleotide comprises at least one of a 2'-O-methoxyethyl sugar moiety, a constrained ethyl sugar moiety, a phosphorothioate internucleoside linkage, or a 5-methylcytosine.

4. A method for the treatment of an HCV infection in a human having an HCV infection according to claim 1, comprising:
administering just once to the human the pharmaceutical composition comprising the long acting parenteral (LAP) HCV active agent of claim 1, in combination with a compound selected from Formula IIA or IIB:

IIB

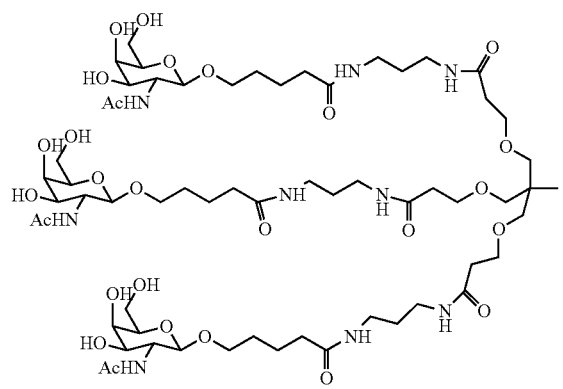

IIA

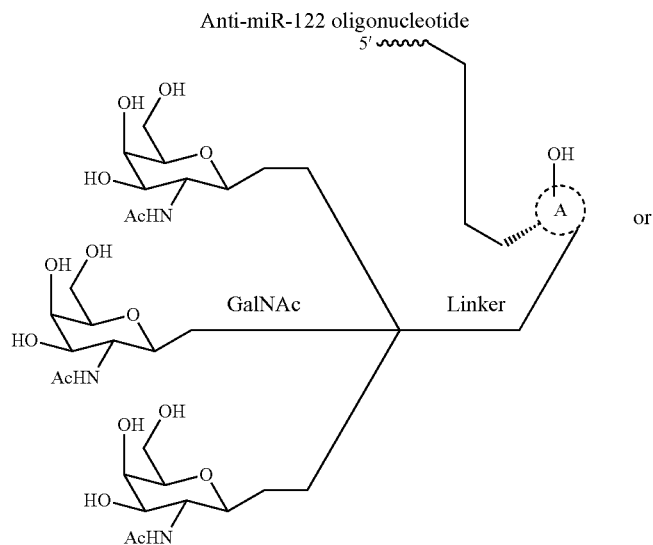

or

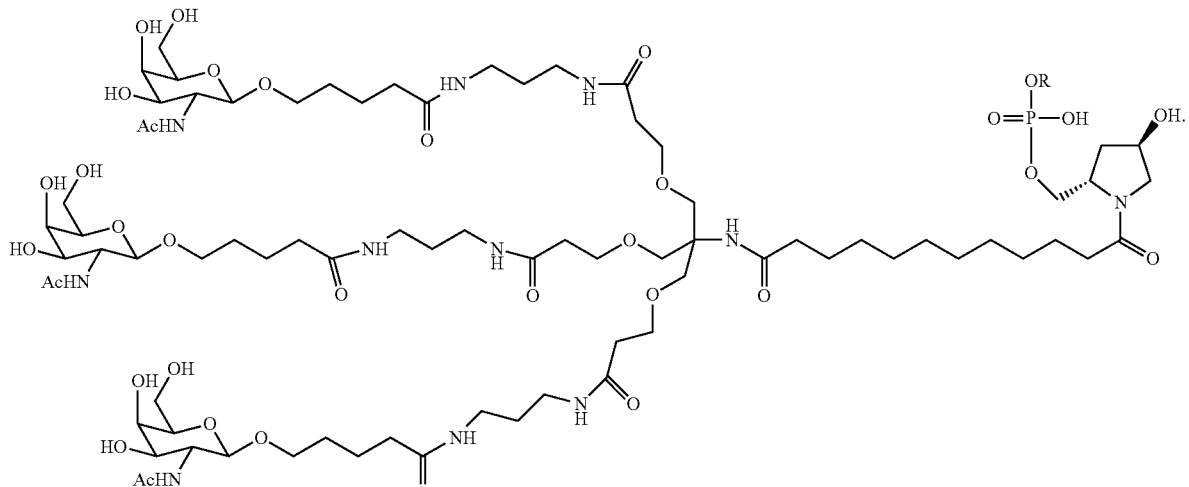

wherein ring A may be independently selected from cycloalkyl or heteroaryl wherein R =

, SEQ ID NO. 1

, or SEQ ID NO. 2

5'-3' anti-miR-122 oligonucleotide-, further comprising a LAP HCV active agent selected from:

Telaprevir (Incivek®), Boceprevir (Victrelis®), ABT-450, Faldaprevir (BI-201335), Asunaprevir (BMS-650032), GS-9256, GS-9857, ABT-493, Vedroprevir (GS-9451), Danoprevir (ITM N-191, RG7227), (Grazoprevir) MK-5172, Vaniprevir (MK-7009), Sovaprevir (ACH-1625), Deldeprevir (Neceprevir) (ACH-2684), Narlaprevir (SCH 900518), Simeprevir (TMC 435), ABT-267,ABT-530, Daclatasvir, Velpatasvir, Ledipasvir, ACH-2928, odalasvir (ACH-3102), PPI-668, AZD-7295, Elbasvir (MK-8742), MK-8408, BMS-986094, MK-3862(IDX-21437), Sofosbuvir, AL-335, GS-0938, Mericitabine, BCX-5191, IDX-184, ALS-2200(VX-135), ALS-2158, TMC649128, VX-222, ABT-072, ABT-333, Deleobuvir (BI-207127), Tegobuvir (GS-9190), Setrobuvir (ANA-598), CC-31244, Filibuvir (PF-868554), VCH-916, VCH-759, BMS-791325, TMC-647055, TKM-HCV, or a pharmaceutically salt thereof.

5. The method according to claim 4, wherein R is a 5'-3' anti-miR-122 oligonucleotide and wherein the anti-miR-122 oligonucleotide comprises at least one modified internucleoside linkage, modified sugar moiety, or modified nucleobase.

6. The method according to claim 4, wherein R is a 5'-3' anti-miR-122 oligonucleotide and wherein the anti-miR-122 oligonucleotide.

7. The method according to claim 1, wherein the LAP pharmaceutical composition further comprises a surfactant system.

8. The method according to claim 7, wherein the surfactant system comprises a surfactant in an amount ranging from about 0.1% (w/v) to about 10% (w/v) surfactant, about 1% (w/v) to about 8% (w/v) surfactant, or about about 2% (w/v) surfactant.

9. The method according to claim 7, wherein the surfactant system comprises a surfactant selected from the group consisting of polyoxyethylene sorbitan fatty acid esters, poloxamers, sorbitan esters of fatty acids (SPAN), polyethoxylated castor oil and its derivatives, tocopheryl polyethylene glycol succinate, and polyvinyl alcohols.

10. The method according to claim 7, wherein the surfactant system comprises a surfactant that is polysorbate 20, polysorbate 80 or polyethylene glycol.

11. The method according to claim 7, wherein the surfactant system comprises a stabilizer that is selected from the group consisting of polyethylene glycols, carboxymethylcellulose calcium, Carboxymethylcellulose sodium, methylcellulose, hydroxyethylcellulose, hydroxypropylcellulose, hydroxymethylpropylcellulose, polysaccharides, hyarluronic acid, polyvinyl alcohol (PVA) and polyvinylpyrrolidone (PVP).

12. The method according to claim 7, wherein the surfactant system comprises a stabilizer that is PEG-3350.

13. The method according to claim 7, wherein the surfactant system comprises a stabilizer in an amount that ranges from about 1% (w/v) to about 5% (w/v) stabilizer or about 2% (w/v) stabilizer.

14. The method according to claim 7, wherein the surfactant system comprises a buffer salt at a concentration of about 10 mM.

15. The method according to claim 14, wherein the surfactant system comprises a buffer salt that is acetate buffered saline.

16. The method according to claim 1, the LAP HCV active agent of claim 1 is in a crystalline form.

17. The method according to claim 16, wherein the LAP HCV active agent of claim 1 is in a crystalline microparticle form.

18. The method according to claim 17, wherein the LAP HCV active agent of claim 1 is in a crystalline microparticle form and wherein the crystalline microparticles of a LAP HCV active agent range in size from about 0.05 µm to about 100 µm, or from about 0.1 µm to about 5 µm.

19. The method according to claim 16, wherein the LAP HCV active agent of claim 1 in the crystalline form prior to encapsulating into a microparticle and combining with a surfactant system.

20. The method according to claim 19, wherein the LAP HCV active agent of claim 1 is encapsulated in a polymer.

21. The method according to claim 20, wherein the LAP HCV active agent of claim 1 is encapsulated in a polymer that comprises poly (lactic-co-glycolic) acid.

22. The method according to claim 1, wherein the human is administered the LAP pharmaceutical composition comprising the LAP HCV active agent of claim 1, on a dosing regimen ranging from about every week to about every three months, on a dosing regimen ranging from about every week to about every two months, on a dosing regimen that is monthly, on a dosing regimen that is only one to two administrations or on a dosing regimen that is only one administration.

23. The method according to claim 22, wherein the administration comprises an injection.

24. The method according to claim 23, wherein the administration comprises an intramuscular injection.

\* \* \* \* \*